US010040747B2

(12) United States Patent
Myllyoja et al.

(10) Patent No.: US 10,040,747 B2
(45) Date of Patent: Aug. 7, 2018

(54) METHOD FOR CATALYTIC CONVERSION OF KETOACIDS AND HYDROTREATMENT TO HYDROCARBONS

(71) Applicant: NESTE OYJ, Espoo (FI)

(72) Inventors: Jukka Myllyoja, Vantaa (FI); Rami Piilola, Helsinki (FI); Maaria Seläntaus, Helsinki (FI); Esko Karvinen, Helsinki (FI)

(73) Assignee: NESTE OYJ, Espoo (FI)

( * ) Notice: Subject to any disclaimer, the term of this patent is extended or adjusted under 35 U.S.C. 154(b) by 0 days.

(21) Appl. No.: 15/010,853

(22) Filed: Jan. 29, 2016

(65) Prior Publication Data

US 2016/0221914 A1 Aug. 4, 2016

(30) Foreign Application Priority Data

Jan. 30, 2015 (EP) .................................. 15153266

(51) Int. Cl.
*C07C 51/353* (2006.01)
*C10G 45/58* (2006.01)
*C10G 3/00* (2006.01)

(52) U.S. Cl.
CPC .............. *C07C 51/353* (2013.01); *C10G 3/50* (2013.01); *C10G 45/58* (2013.01); *Y02P 30/20* (2015.11)

(58) Field of Classification Search
CPC ... C07C 51/373; C07C 51/353; C07C 59/347; C07C 51/377; C07C 59/76; C07C 5/2767; C07C 1/2078; C10G 45/58; C10G 3/50; Y02P 30/20

See application file for complete search history.

(56) References Cited

U.S. PATENT DOCUMENTS

| 2006/0135793 | A1 | 6/2006 | Blessing et al. |
| 2012/0203043 | A1 | 8/2012 | Wheeler et al. |
| 2012/0283493 | A1* | 11/2012 | Olson ................ C10L 1/08 585/242 |
| 2016/0221912 | A1* | 8/2016 | Myllyoja .............. C07C 51/377 |

FOREIGN PATENT DOCUMENTS

| RU | 2182163 C2 | 5/2002 |
| WO | WO 2006/056591 A1 | 6/2006 |

OTHER PUBLICATIONS

Amarasekara ("NaOH catalyzed condensation reactions between levulinic acid and biomass derived furan-aldehydes in water" Industrial Crops and Products, 65, first available online Oct. 22, 2014, p. 546-549).*
Chieh ("Strong Acids and Bases" < http://www.science.uwaterloo.ca/~cchieh/cact/c123/stacids.html >, downloaded on Jan. 20, 2017, p. 1-5).*

(Continued)

*Primary Examiner* — Jafar Parsa
*Assistant Examiner* — Amy C Bonaparte
(74) *Attorney, Agent, or Firm* — Buchanan Ingersoll & Rooney PC

(57) ABSTRACT

The present invention relates to catalytic conversion of ketoacids, including methods for increasing the molecular weight of ketoacids, the method can include providing in a reactor a feedstock comprising at least one ketoacid, water and a base. The feedstock is then subjected to base catalysed condensation reactions.

26 Claims, 3 Drawing Sheets

(56) References Cited

OTHER PUBLICATIONS

Levulinic Acid (< https://pubchem.ncbi.nlm.nih.gov/compound/4-Oxopentanoic_acid#section=Physical-Description>, downloaded on Jan. 20, 2017, p. 1-28).*

Climent ("Conversion of biomass platform molecules into fuel additives and liquid hydrocarbon fuels" Green Chemistry, 2014, 16, 516—published online Oct. 23, 2013).*

Carey ("Chapter 2: Reactions of Nucleophilic Carbon Species with Carbonyl Groups" Advanced Organic Chemistry, Part B: Reactions and Synthesis, 1977, p. 33-71).*

UCLA (http://www.chem.ucla.edu/~harding/notes/notes_14D_C=Ofun03.pdf, downloaded on Aug. 30, 2017, p. 1-11).*

European Search Report dated Jul. 17, 2015.

Serrano-Ruiz et al. "Conversion of Cellulose to Hydrocarbon Fuels by Progressive Removal of Oxygen", Applied Catalysis B: Environmental, Oct. 11, 2010, vol. 100, No. 1-2, pp. 184-189, XP-027358402.

Mascal El Al., "Hydrodeoxygenation of the Angelica Lactone Dimer, a Cellulose-Based Feedstock: Simple, High-Yield Synthesis of Branched C7-C10 Gasoline-like Hydrocarbons," Angew. Chem., 2014, 126, pp. 1885-1888.

Office Action issued by the Russian Patent Office in a corresponding Russian Patent Application dated May 30, 2017.

* cited by examiner

Figure 1 – Conversion of lignocellulosic material to levulinic acid
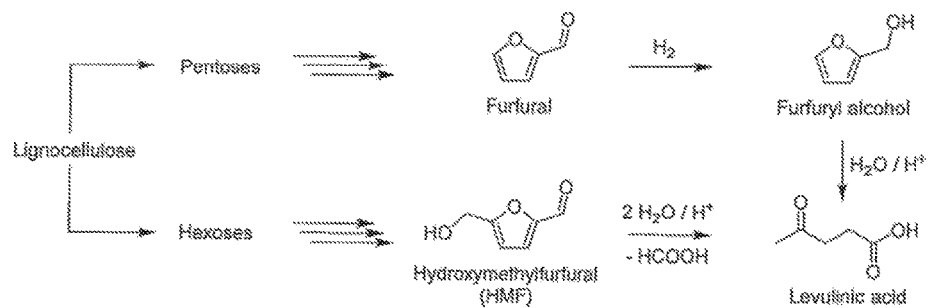
Figure 2 – Reaction products of levulinic acid
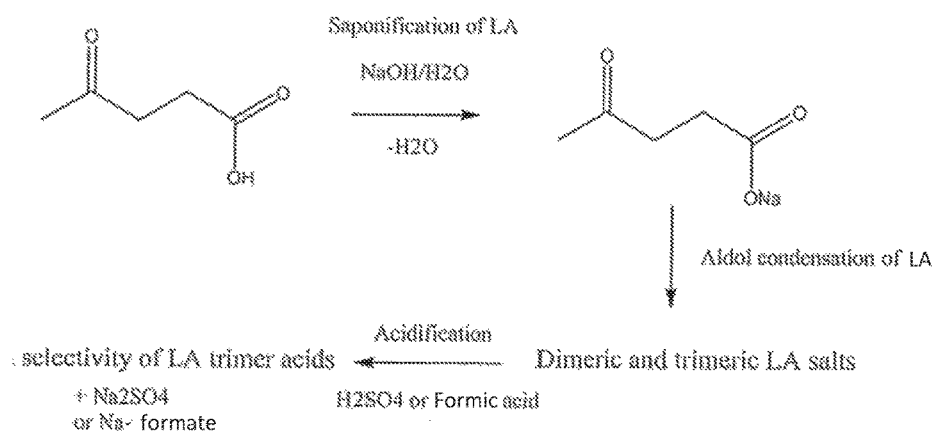

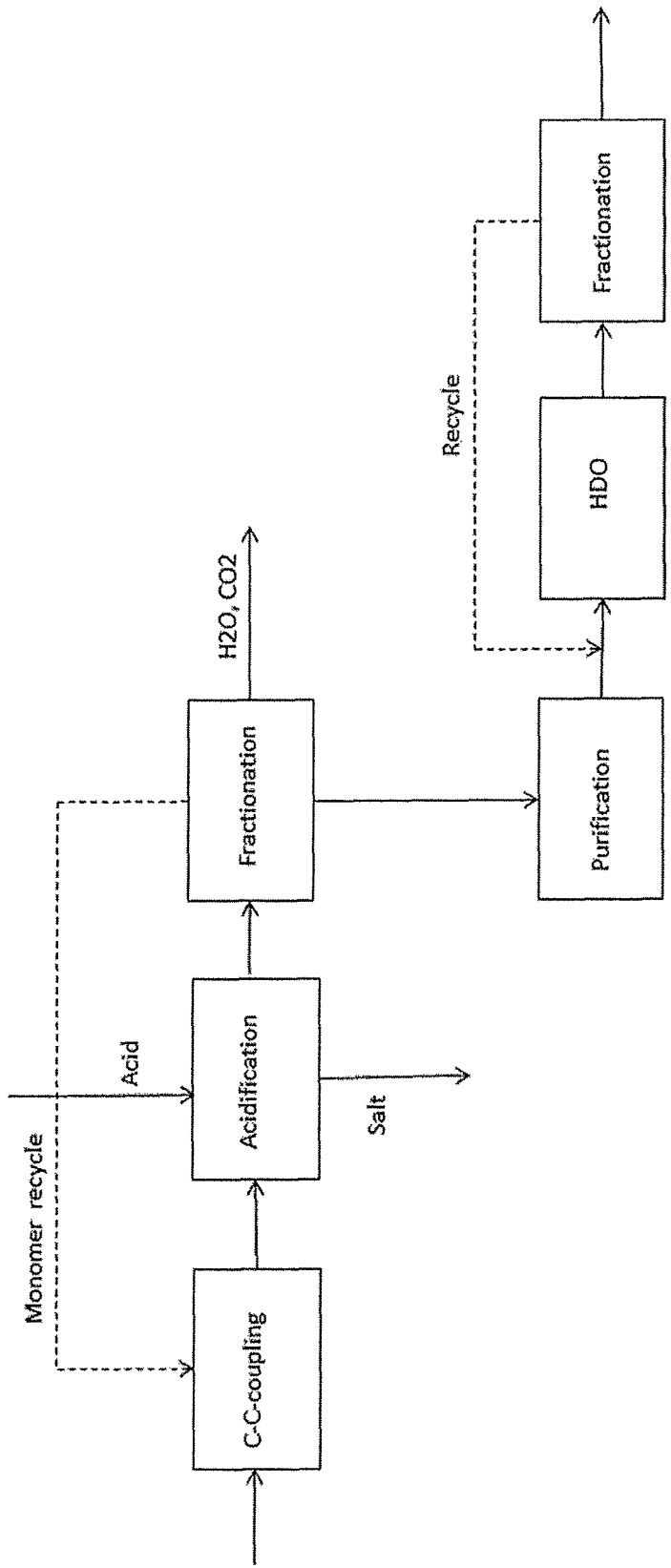
Figure 3 – Process scheme for upgrading C-C coupling reactions

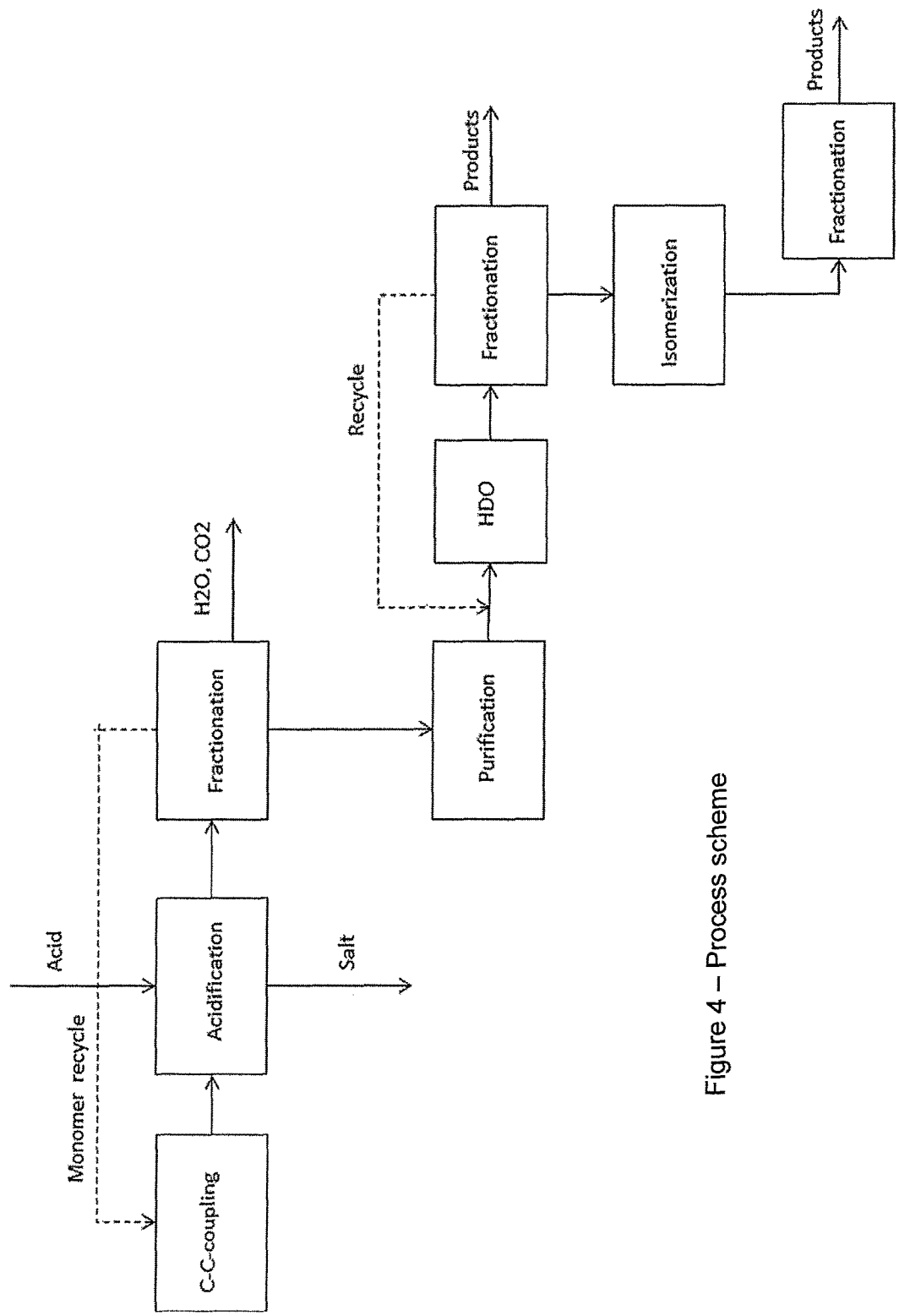
Figure 4 – Process scheme

METHOD FOR CATALYTIC CONVERSION OF KETOACIDS AND HYDROTREATMENT TO HYDROCARBONS

TECHNICAL FIELD

The present invention relates to catalytic conversion of ketoacids, including methods for increasing the molecular weight of ketoacids, products obtainable by such methods, as well as use of such products for the production of liquid hydrocarbons and/or gasoline or diesel fuel or base oil components.

BACKGROUND ART

Production of hydrocarbons used as fuel or base oil components and chemicals from biomass are of increasing interests since they are produced from a sustainable source of organic compounds.

The ketoacid Levulinic acid (LA, 4-oxopentanoic acid) is one of many platform molecules that may be derived from biomass. It may be produced from both pentoses and hexoses of lignocellulosic material (see FIG. 1) at relatively low cost. Some of the advantages and drawbacks of using levulinic acid as a platform molecule relate to the fact that it is considered to be a reactive molecule due to both its keto and acid functionality.

Esters of levulinic acid have been suggested as fuel components as well as cold flow additives in diesel fuels, and in particular the methyl and ethyl esters have been used as additives in diesel fuel. Gamma-valerolactone (GVL), which may be obtained by reduction of levulinic acid, has been used as a fuel additive in gasoline. Further reduction of GVL to 2-methyltetrahydrofuran (MTHF) provides a product that may be blended with gasoline of up to 60%. Alkyl valerates produced from levulinic acid have also been suggested as biofuels.

Levulinic acid has also been used for the production of liquid hydrocarbon fuels by a number of catalytic routes, including a method of producing a distribution of alkenes, the distribution centered around $C_{12}$, involving converting aqueous GVL in a first reactor system to butenes followed by oligomerization in a second reactor over an acidic catalyst (e.g. Amberlyst® 70).

Serrano-Ruiz et al. (*Appl. Catal., B*, 2010, 100, 184) produced a $C_9$-ketone (5-nonanone) by reducing levulinic acid to GVL over a Ru/C catalyst in one reactor followed by reacting 40 wt % GVL in water and 0.02 M $H_2SO_4$ in a Pd/$Nb_2O_5$+ceria-zirconia double bed arrangement at 325-425° C., 14 bar, WHSV=0.8–0.5 $h^{-1}$ in another reactor. Using multiple reactors may be advantageous as it can offer more control over the process compared to using a single reactor. However, multiple reactors increase the number of process steps, which increases the capital expenditure of the process.

US 2006/0135793 A1 (to Blessing and Petrus) disclose dimerization of levulinic acid to a $C_{10}$ unit in the presence of hydrogen, with a strong acidic heterogenous catalyst, e.g. ion exchange resin catalyst, comprising a hydrogenating metal, at a temperature in the range from 60 to 170° C. and a pressure of 1 to 200 bar (absolute). The example indicates as main products levulinic acid dimers (26%) and unreacted levulinic acid (70%). Relatively low reaction temperatures are preferred due to the thermal instability of ion exchange resins at temperatures of above 150° C.

US 2012/203043 A1 discloses a method, in which a feedstock comprising levulinic acid salt of is mixed with a formic acid salt and the mixture is subjected to a thermal deoxygenation reaction at a temperature of 200-600° C. to obtain hydrocarbon vapor, which is condensed to liquid hydrocarbons

SUMMARY OF INVENTION

Upgrading levulinic acid and other ketoacids to higher molecular weight compounds can be achieved through reaction routes involving single or multiple reaction steps, both of which have certain advantages and disadvantages. Using a single reactor compared to multiple reactors may be advantageous in that they reduce the number of process steps and therefore increase the process economy. Some of the drawbacks associated with direct routes of upgrading e.g. using single reactors are that these reactions generate highly reactive intermediates with more than one functional group, which can further react to other undesired molecules. Reduction of undesired molecules by direct routes of upgrading usually entails a lower yield of the desired product composition. Usually the suppression of side reactions producing undesired molecules is accomplished by using dilute aqueous solutions of levulinic acid as a feedstock. Accordingly, an indirect route of upgrading a feedstock using multiple reactors or multiple catalyst beds in a single reactor may in some situations be preferred compared to a direct route of upgrading.

Consequently, there is a need for additional processes for upgrading levulinic acid and other ketoacids to higher molecular weight compounds, which are suitable for use as e.g. fuel or base oil components or chemicals or as components in the production of fuel or base oil components or chemicals. In particular, there is a need for such additional processes, which reduce the processing costs by I.a. improving the yield of the desired components.

The present invention was made in view of the prior art described above, and one of the objects of the present invention is to provide methods that enable upgrading of ketoacids via improved routes to higher molecular weight compounds.

Another object of the present invention is to provide the upgrade of ketoacids to higher molecular weight compounds in good yield and at low processing costs.

The higher molecular weight compounds produced with the method of the present invention are especially suitable for use as fuel or base oil components or chemicals or as starting materials in production of these.

Thus the present invention provides a method for increasing the molecular weight of a ketoacid as defined in claim 1.

In the step of subjecting the feedstock to one or more base catalysed condensation reaction(s), the at least one ketoacid undergoes at least one condensation reaction with another ketoacid or ketoacid derivative present in the feedstock so as to increase the molecular weight of the ketoacid. The ketoacids participating in the condensation reaction(s) may be of the same type (having the same chemical formula) or of a different type. The ketoacid derivate includes all compounds directly obtainable from a ketoacid through condensation reactions. The ketoacid derivatives may be selected from the list consisting of lactones, lactone derivatives of ketoacids and ketoacid dimers and oligomers obtained from ketoacids through condensation reactions.

In a base catalyzed condensation reaction the at least one ketoacid reacts with another reactant with the formation of a new carbon-carbon bond in the product. The base catalysed condensation reaction may be selected from a list comprising aldol type condensations, Michael addition and reactions between esters and di-esters such as Claisen condensation or Dieckmann condensation. In other words, the molecular weight of the ketoacid is increased using the ketoacid as a direct precursor (one-step reaction) in a reactor. As a matter of course, further base catalysed condensation reactions may occur so as to further increase the molecular weight the condensation reaction product. These further reactions are preferably conducted in the same (single) reactor.

The at least one ketoacid is preferably a γ-ketoacid, most preferably levulinic acid. The at least one ketoacid may be a mixture of different ketoacids.

The reactor employed in the method of the present invention may be a stirred tank reactor, preferably a continuous stirred tank reactor or a tubular flow reactor, preferably a continuous flow reactor. A continuous stirred tank reactor is preferred from the viewpoint of production efficiency.

There are several bases, which may be used in the base catalysed condensation reactions of ketoacids. Preferably the base is a hydroxide, carbonate, or phosphate of an alkaline metal or alkaline earth metal, preferably a hydroxide, carbonate, or phosphate of one of Na, Li, Be, Mg, K, Ca, Sr, or Ba or any combination of these.

Preferably, the base is sodium hydroxide, potassium hydroxide or lithium hydroxide or any combination of these. Preferably, the base is a mixture of a hydroxide of sodium, potassium or lithium and a further metal hydroxide.

The base catalysed condensation reaction(s) can be controlled by adjusting several parameters, including by selection of reaction conditions such as temperature and pressure.

Preferably, the base catalysed condensation reactions are conducted at a temperature of at least 65° C., preferably at a temperature in the range of 70 to 195° C., more preferably at a temperature in the range of 80 to 160° C., even more preferably at a temperature in the range of 90 to 140° C. and most preferably at a temperature in the range of 100 to 120° C. This temperature range was found to be particularly suitable for obtaining a high degree of medium molecular weight reaction products such as ketoacid trimers.

Preferably, the base catalysed condensation reactions are conducted at a pressure in the range of 1.00-30.0 bar, preferably 1.05-20.0 bar, more preferably 1.10-10.0 bar (absolute).

The required amount of the base depends on the content of ketoacid(s) in the feedstock. Preferably, the content of the base in the feedstock adjusted such that that the pH of the feedstock is at least 8.0, preferably at least 10.0, more preferably at least 12.0.

Preferably the molar ratio of the content of the base in the feedstock is adjusted such that the number of proton accepting groups provided by the base to the number of carboxylic acid groups provided by the at least one ketoacid is in the range of 1.0:1.0 to 5.0:1.0, preferably 1.05:1.0 to 2.0:1.0. If the feedstock comprises two or more bases, "the content of the base" refers to the total content of all bases.

Preferably, the molar ratio of the content of the base in the feedstock to the content of the at least one ketoacid in the feedstock is in the range of 1.00:1.00 to 5.00:1.00, preferably 1.05:1.00 to 3.00:1.00, even more preferably 1.10:1.00 to 2.00:1.00. In calculating the molar ratio, the molar amount of the base is calculated as molar amount of the corresponding monohydric base. For example, in calculating the molar ratio of the content of $Ca(OH)_2$ in the feedstock to the content of ketoacid, the molar amount of the $Ca(OH)_2$ is multiplied by two due to the presence of two hydroxide groups per one molecule of the base.

The inventors of the present invention have found that the base catalysed condensation reactions between ketoacids start to occur when most of the carboxylic acid groups of the ketoacids have been deprotonated with the base present in the feedstock. Preferably, the content of the base in the feedstock is adjusted such that more than 90% (by mole), preferably more than 95%, more preferably more than 99%, of the acid groups of the at least one ketoacid in the feedstock are deprotonated.

Preferably, the acid groups of the at least one ketoacid in the feedstock are converted into carboxylic acid metal salt groups.

The invention provides a method for industrial scale production of higher molecular weight products of ketoacids and, therefore, the base catalysed condensation reactions are preferably conducted using a feedstock having a high concentration of ketoacids. Preferably, the content of the at least one ketoacid in the feedstock is at least 5 mol-%, preferably at least 10 mol-%, more preferably at least 15 mol-%, even more preferably at least 20 mol-%. If multiple ketoacids are present in the feedstock, the "content of the at least one ketoacid" refers to the total content of all ketoacids.

In this respect, it is to be noted that the term "feedstock" in the present invention includes all material fed into the reactor. Thus, the calculation of the content of the at least one ketoacid in the feedstock does not consider the amount of compounds formed in any reactions after preparing the feedstock.

The content of water in the feedstock is preferably at least 1 mol-%, preferably at least 10 mol-%, more preferably a least 20 mol-%, even more preferably at least 30 mol-%.

The presence of water in the feedstock has been found to increase the yield of the desired C-C-coupling reaction products and to decrease the reactions to high molecular weight polymer compounds, which cannot be used in fuel, base oil or chemical applications.

Preferably, the feedstock comprises 5.0-40.0 mol-% alkaline metal hydroxide or alkaline earth metal hydroxide, preferably 1.0-70.0 mol-% water, and preferably 5.0-40.0 mol-% of the at least one ketoacid.

In the present invention, the base is used to convert the carboxylic acid groups of the at least ketoacid into salt form. Without being bound to any theory, this is suggested to prevent internal esterification and formation of unreactive lactone groups in ketoacids. The base is suggested to catalyse the condensation reactions, especially aldol condensation reactions of the carbonyl group of the at least one ketoacid. In the present invention, the base catalyst is suitably a catalyst for homogenous catalysis.

Preferably a mixture of at least two basic compounds is used as the base.

Preferably, the method of the present invention further comprises a step of preparing the feedstock by mixing the at least one ketoacid, the base and optionally the water prior to subjecting the feedstock to the base catalysed condensation reaction(s). The step of preparing the feedstock is preferably conducted at a temperature in the range of 10° C. to 55° C., preferably 15° C. to 45° C. The temperature refers to the initial temperature, i.e. at the beginning of the mixing operation. The feedstock may be heated to a desired reaction temperature before subjecting it to base catalysed condensation reactions.

After conducting the base catalysed condensation reaction(s), the produced reaction product comprising dimers, trimers and other oligomers of ketoacid(s) is still in salt form. The metal ions are preferably removed from the reaction products before further utilization of the reaction product as fuel, base oil components or as starting materials in production of these.

Preferably, the method of the present invention comprises a further step of acidifying the reaction product of the condensation reaction(s) by adding an acid.

The acid is added to the reaction product at least in amount sufficient to convert at least 95% (by mole), preferably 100% of the carboxylic acid metal salt groups into carboxylic acid groups.

An inorganic acid or organic acid may be used in the acidifying step.

Preferably an organic acid is used, more preferably formic acid or acetic acid.

Preferably the base is sodium hydroxide, potassium hydroxide or lithium hydroxide and the organic acid is formic acid.

Preferably, the method of the present invention comprises a further step of purifying the acidified C-C-coupling reaction products by extraction, precipitation or crystallization, preferably by liquid-liquid extraction using a solvent.

In a further aspect of the present invention, a reaction product obtainable by the method according to the present invention is provided.

In another aspect of the present invention, a method for producing hydrocarbons from a feedstock comprising at least one ketoacid is provided.

In still another aspect of the present invention, a hydrocarbon composition obtainable by the method according to the present invention is provided.

In brief, the present invention relates to one or more of the following items:

1. A method for increasing the molecular weight of a ketoacid, the method comprising providing in a reactor a feedstock comprising at least one ketoacid, water and a base, and subjecting the feedstock to one or more base catalysed condensation reaction(s).
2. The method according to item 1, wherein the at least one ketoacid is a γ-ketoacid, preferably levulinic acid.
3. The method according to item 1 or 2, wherein the base is a hydroxide, carbonate, or phosphate of an alkaline metal or alkaline earth metal, preferably a hydroxide, carbonate, or phosphate of one of Na, Li, Be, Mg, K, Ca, Sr or Ba, or a combination of these.
4. The method according to any of items 1-3, wherein the base is sodium hydroxide, potassium hydroxide or lithium hydroxide or a combination of these.
5. The method according to any of items 1-4, wherein the C-C-coupling reactions are conducted at a temperature of at least 65° C., preferably at a temperature in the range of 70 to 195° C., more preferably at a temperature in the range of 80 to 160° C., even more preferably at a temperature in the range of 90 to 140° C. and most preferably at a temperature in the range of 100 to 120° C.
6. The method according to any of items 1-5, wherein the C-C-coupling reactions are conducted at a pressure of 1.00-30.00 bar, preferably 1.05-20.00 bar, more preferably 1.10-10.00 bar.
7. The method according to any of items 1-6, wherein the content of the base in the feedstock adjusted such that that the pH of the feedstock is at least 8.0, preferably at least 10.0, more preferably at least 12.0.
8. The method according to any of items 1 to 7, wherein the content of the base in the feedstock is adjusted such that the ratio of the number of proton accepting groups provided by the base to the number of carboxylic acid groups provided by the at least one ketoacid is in the range of 1.00:1.00 to 5.00:1.00, preferably 1.05:1.00 to 2.00:1.00.
9. The method according to any of items 1 to 8, wherein the molar ratio of the content of the base in the feedstock to the content of the at least one ketoacid in the feedstock is in the range of 1.00:1.00 to 5.00:1.00, preferably 1.05:1.00 to 3.00:1.00 even more preferably 1.10:1.00 to 2.00:1.00.
10. The method according to any of items 1 to 9, wherein the content of the base in the feedstock is adjusted such that more than 90% (by mole), preferably more than 95%, more preferably more than 99%, of the acid groups of the at least one ketoacid in the feedstock are deprotonated.
11. The method according to item 10, wherein the acid groups of the at least one ketoacid in the feedstock are converted into carboxylic acid metal salt groups.
12. The method according to any of the items 1-11, wherein the content of the at least one ketoacid in the feedstock is at least 5.0 mol-%, preferably at least 10.0 mol-%, more preferably at least 15.0 mol-%, even more preferably at least 20.0 mol-%.
13. The method according to any of the items 1-12, wherein the content of water in the feedstock is at least 1.0 mol-%, preferably at least 10.0 mol-%, more preferably a least 20.0 mol-%, even more preferably at least 30.0 mol-%.
14. The method according to any of items 1-13, wherein the feedstock comprises 5.0-40.0 mol-% alkaline metal hydroxide or alkaline earth metal hydroxide, preferably 1.0-70.0 mol-% water and preferably 5.0-40.0 mol-% of the at least one ketoacid.
15. The method according to any of items 1-14, wherein a mixture of at least two basic compounds is used as the base.
16. The method according to any of items 1-15, wherein the method further comprises a step of preparing the feedstock by mixing the at least one ketoacid, the base and optionally the water prior to subjecting the feedstock to the one or more base catalysed condensation reaction(s).
17. The method according to any of item 16, wherein the step of preparing the feedstock is conducted at a temperature in the range of 10° C. to 55° C., preferably 15° C. to 45° C.
18. The method according to any of items 1-17, wherein the method comprises a further step of acidifying the reaction product of the condensation reaction(s) by adding an acid.
19. The method according to item 18, wherein the acid is an inorganic acid or an organic acid.
20. The method according to any of items 18 or 19, wherein the acid is an organic acid, preferably formic acid or acetic acid.
21. The method according to any of items 18-20, wherein the base is sodium hydroxide, potassium hydroxide or lithium hydroxide and the acid is formic acid.
22. The method according to any of items 18-21, wherein the method comprises a further step of purifying the acidified reaction product by extraction, precipitation or crystallization, preferably by liquid-liquid extraction using a solvent.
23. A reaction product obtainable by the method according to any of items 1-22.
24. A method of producing hydrocarbons, the method comprising the steps of increasing the molecular weight of a ketoacid using the method according to any of items 18-22 to obtain a reaction product and subjecting the reaction product to a hydrodeoxygenation step and optionally to an isomerization step.
25. A hydrocarbon composition obtainable by the method according to item 24.

BRIEF DESCRIPTION OF DRAWINGS

FIG. 1 shows a scheme illustrating conversion of lignocellulosic material to levulinic acid.

FIG. 2 shows a scheme illustrating one possible reaction route used in the present invention. The figure is not intended to cover all condensation reaction products of levulinic acid. In the reaction route of FIG. 2, sodium hydroxide is used as the base and the condensation reaction product is acidified with sulphuric acid.

FIG. 3 shows an overview of a possible process scheme for preparing and further upgrading the products from the base catalysed condensation reactions.

FIG. 4 shows an overview of another possible process scheme for preparing and upgrading the products from the base catalysed condensation reactions.

DETAILED DESCRIPTION OF THE INVENTION

One of the challenges in increasing the molecular weight of ketoacids by C-C-coupling reactions is the high reactivity of the product intermediates, which results in too high a degree of oligomerisation of the starting components.

The inventors have found that the oligomerisation of a ketoacid, specifically of levulinic acid, in the presence of a typical ketonisation catalyst such as $K_2O/TiO_2$ results in high formation of coke and tar, which poison the catalyst by blocking the reactive sites on the surface of the catalyst and eventually result in plugging of the reactor. Without being bound to any theory this is suggested to occur due to reactions of levulinic acid to more reactive precursors such as angelica lactones, which are known to have a high tendency to polymerise at high temperatures of over 200° C. required for heterogeneous catalysis using a ketonization catalyst.

The invention is based on a surprising finding that the molecular weight of ketoacids can be selectively increased by converting most of the carboxylic acid groups of the ketoacids to metal salt groups and subsequently subjecting the ketoacids to one or more base catalyzed condensation reaction(s) in the presence of water and a base. Without being bound to any theory it is suggested that converting the carboxylic acid groups to metal salt groups prevents internal esterification of ketoacids to lactones and decreases the formation of unreactive lactone groups. Saponification of the carboxylic acid groups has been found to increase the selectivity of base catalysed condensation reactions of ketoacids to trimers and other oligomers suitable for use as fuel or base oil components or chemicals or starting materials in production of these. Ketoacids with saponified carboxylic acid groups have been found to form trimers and other desired oligomers in the presence of a base catalyst.

Accordingly, one aspect the present invention is a method for increasing the molecular weight of a ketoacid, the method comprising the steps of providing in a reactor a feedstock comprising at least one ketoacid, water and a base and subjecting the feedstock to one or more base catalysed condensation reaction(s).

The present invention also relates to a method for increasing the molecular weight of ketoacids.

Ketoacids are organic molecules that have both a keto function ($>C=O$) as well as a carboxylic acid (COOH) or carboxylate ($COO^-$) function.

The ketoacid may for example be an alpha-ketoacid (such as pyruvic acid, oxaloacetic acid and alpha-ketoglutaric acid), beta-ketoacid (such as acetoacetic acid), gamma-ketoacid (such as levulinic acid), or delta-ketoacid. The ketoacid may have more than one keto functionality, and more than one carboxylic acid function. Preferably, the ketoacid only has one keto functionality and one carboxylic acid functionality.

Scheme 1

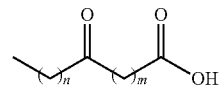

Scheme 1 illustrates exemplary ketoacids according to the present invention, for example where n and m are integers each selected independently of each other from the list consisting of 0, 1, 2, 3, 4, 5, 6, 7, 8, 9, 10. Preferably, the ketoacid is a gamma ketoacid, more preferably levulinic acid (m=2, n=0).

Preferably, the molecular weight of the ketoacids in the feedstock is increased by at least 80% or more by the method of the present invention. Preferably, the molecular weight is increased to be from 150 to 1000 g/mol, such as 160 to 800 g/mol. Where the ketoacid is a C4-C7-ketoacid, the molecular weight may be increased to corresponding molecules having a C8-C35 carbon chain, such as a C8-C30 carbon chain.

Preferably, more than 40 wt % of the reaction product belong to the group containing dimerization, trimerisation, tetramerisation, pentamerisation, and hexamerisation products of ketoacid. By dimerization, trimerisation, tetramerisation, pentamerisation and hexamerisation products is meant reaction products relating to two, three, four, five and six molecules of one or more of ketoacids being coupled together, respectively. In the case of a feedstock comprising derivatives of ketoacids in addition to ketoacids, the dimerization, trimerisation, tetramerisation, pentamerisation, and hexamerisation products may additionally contain mixed condensation products comprising one or more ketoacids and/or derivatives thereof. Examples of ketoacid trimers according to the invention are shown by the following formulas, using levulinic acid trimers as examples:

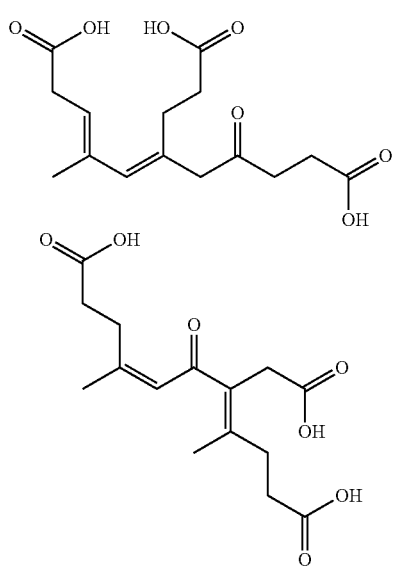

-continued

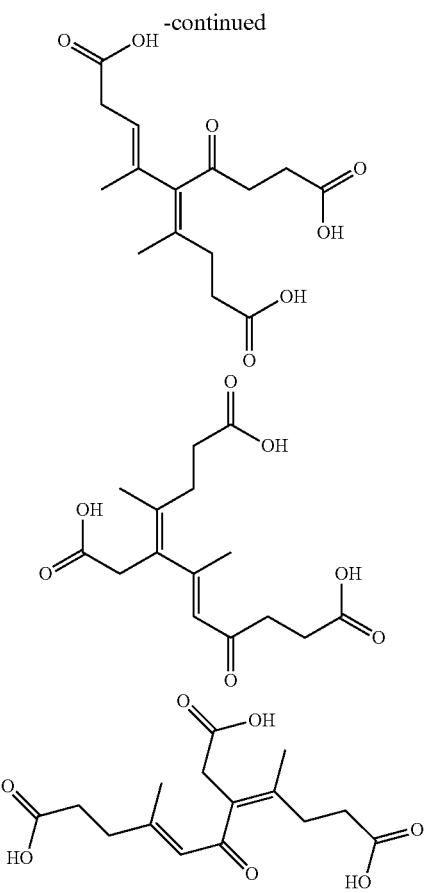

In the present invention the molecular weight of the keto acids are increased through one or more types of base catalysed condensation reaction(s). Many types of base catalysed condensation reactions are known in the art, and the skilled person would be able to identify such condensation reactions based on the reaction conditions provided. In the present invention, the base catalysed condensation reactions are predominantly aldol condensation and Michael addition reactions but some other condensations such as Claisen or Dieckmann condensations may also occur. Aldol and Michael condensations are most likely to occur in the employed reaction conditions since the saponification of the carboxylic acid group prevents reactions involving the acid groups.

The base catalysed condensation reactions may proceed with two identical types of molecules (i.e. the same compound) or may be a crossed reaction between two different types of molecules (i.e. between different compounds).

The at least one ketoacid preferably contains a γ-ketoacid, most preferably levulinic acid. In addition, one or more further ketoacids and/or ketoacid derivatives may be employed.

The feedstock may comprise a mixture of levulinic acid in combination with ketoacid derivatives, such as at least 30 mol-% of levulinic acid and at least 10 mol-% of levulinic acid derivative(s) based on the total molar amount of feedstock.

In addition to ketoacids and ketoacid derivatives, the feedstock may also contain aldehydes, such as furfural or hydroxymethylfurfural.

The feedstock may be obtained from processing of lignocellulosic material, and such processed material may be used directly, or purified to varying degrees before being used as a feedstock in the method of the present invention. The levulinic acid may be produced e.g. with the Biofine method disclosed in U.S. Pat. No. 5,608,105.

Preferably, the feedstock is provided in a single reactor. The reactor should be able to be pressurised, and to accommodate the feedstock. The reactor should have means, such as one or more inlets and/or outlets, for supplying gases and adding/withdrawing feedstock. In addition, means for controlling the pressure and temperature are preferably present.

There are several bases which can be used in the base catalysed condensation reactions of ketoacids. Preferably the base is a hydroxide, carbonate, or phosphate of an alkaline metal or alkaline earth metal, preferably a hydroxide, carbonate, or phosphate of one of Na, Li, Be, Mg, K, Ca, Sr, or Ba or a combination of these.

Preferably, the base is sodium hydroxide, potassium hydroxide or lithium hydroxide or a combination of these. These bases were found to be particularly suitable for obtaining a high degree of base catalysed condensation reaction products of medium molecular weight (C15-C30) at the reaction temperatures used in the present invention. If more than one basic substance is used as the base, the basic substance used for deprotonating the ketoacid is preferably a metal hydroxide, more preferably sodium hydroxide, potassium hydroxide or lithium hydroxide, and the basic substance used for (further) basifying the feedstock may be any other basic substance different from the basic substance used for deprotonating the ketoacid, preferably a metal hydroxyide.

If a combination of a first and a second basic substance is used as said base, the first basic substance may be used to deprotonate the acid groups in the feedstock after which the second basic substance may be added to the feedstock as base catalyst. Preferably, the molar ratio of the content of the first basic substance to the second basic substance is in the range of 10.0:1.0 to 1.0:1.0, more preferably 5.0:1.0 to 1.5:1.0, even more preferably 3.0:1.0 to 2.0:1.0.

Preferably, the C-C-coupling reactions are conducted at a temperature of at least 65° C., preferably at a temperature in the range of 70 to 195° C., more preferably at a temperature in the range of 80 to 160° C., even more preferably at a temperature in the range of 90 to 140° C. and most preferably at a temperature in the range of 100 to 120° C. This temperature range was found to be particularly suitable for obtaining a high degree of reaction products of medium molecular weight (C10-C30) while still avoiding excessive polymerization of the reactive intermediates.

Preferably, the C-C-coupling reactions are conducted at a pressure of 1.00-30.00 bar, preferably 1.05-20.00 bar, more preferably 1.10-10.00 bar.

The required amount of the base in the feedstock depends on the content of ketoacid(s) in the feedstock. Preferably, the content of the base in the feedstock adjusted such that that the pH of the feedstock is at least 8.0, preferably at least 10.0, more preferably at least 12.0.

Preferably the content of the in base the feedstock is adjusted such that the ratio of the number of proton accepting groups provided by the base to the number of carboxylic acid groups provided by the at least one ketoacid is in the range of 1.00:1.00 to 5.00:1.00, preferably 1.05:1.00 to 2.00:1.00.

Preferably, the molar ratio of the content of the base in the feedstock to the content of the at least one ketoacid in the feedstock is in the range of 1.00:1.00 to 5.00:1.00, preferably 1.05:1.00 to 3.00:1.00 even more preferably 1.10:1.00 to 2.00:1.00.

Preferably, the content of the base in the feedstock is adjusted such that more than 90% (by mole), preferably more than 95%, more preferably more than 99%, of the acid groups of the at least one ketoacid in the feedstock are deprotonated.

Preferably, the acid groups of the at least one ketoacid in the feedstock are converted into carboxylic acid metal salt groups.

The conversion of ketoacid to desired condensation reaction products was found to increase as the content of ketoacid in the feedstock increased. The yield of the base catalysed condensation products has to be high enough to enable an economically feasible process for production of fuel components and chemicals from ketoacids.

Preferably, the content of the at least one ketoacid in the feedstock is at least 5 mol-%, preferably at least 10 mol-%, more preferably at least 15 mol-%, even more preferably at least 20 mol-%.

The content of water in the feedstock is preferably at least 1.0 mol-%, preferably at least 10.0 mol-%, more preferably a least 20.0 mol-%, even more preferably at least 30.0 mol-%. Preferably, the feedstock comprises 5.0-40.0 mol-% alkaline metal hydroxide or alkaline earth metal hydroxide, preferably 1.0-70.0 mol-% water, and preferably 5.0-40.0 mol-% of the at least one ketoacid.

In the step of preparing the feedstock, the base may fed to a reactor already containing the at least one ketoacid and/or water. The base may be added to the reactor as solid in form of pellets, flakes or granulates or as an aqueous solution. Preferably the base is added to the reactor as an aqueous solution. If the base is added to the reactor as a solid, it is preferably dissolved in water present in the feedstock before subjecting the feedstock to the base catalysed condensation reaction(s).

Preferably, the step of preparing the feedstock is conducted at a temperature in the range of 10° C. to 55° C., preferably 15° C. to 45° C. The feedstock may be heated to a desired reaction temperature before subjecting it to the base catalysed condensation reaction(s). Since the dissolving of a solid base such as sodium hydroxide in water is an exothermic reaction producing considerable amount of heat, the feedstock may reach the desired reaction temperature without or with very small amount of external heating.

Preferably, the method of the present invention comprises a further step of acidifying the reaction product of the condensation reaction(s) by adding an acid. The acid is added to the reaction product at least in an amount sufficient to convert at least 95% (by mole), preferably 100% of the carboxylic acid metal salt groups into carboxylic acid groups. If the reaction product is used as a starting material for production of hydrocarbons, all the carboxylic acid metal salt groups are preferably desaponified before removal of oxygen since the hydrodeoxygenation catalyst are prone to deactivation in the presence of metals.

An inorganic acid or organic acid may be used in the acidifying step.

Preferably an organic acid is used, more preferably formic acid or acetic acid.

Preferably the base is sodium hydroxide, potassium hydroxide or lithium hydroxide and the organic acid is formic acid.

After the acidification, the reaction product has to be separated from the mixture. Preferably, the method of the present invention comprises a further step of purifying the acidified reaction product by extraction, precipitation or crystallization, preferably by liquid-liquid extraction using a solvent.

In another aspect of the present invention, a reaction product obtainable by the method according to the present invention is provided. The product may be used directly as fuel or base oil component or chemicals or as intermediate components in production of fuel or base oil components or chemicals.

The purified reaction product obtainable by the method of the present invention may—if desired—be further subjected to a hydrodeoxygenation (HDO) step to remove oxygen, which preferably produces completely deoxygenated material (i.e. hydrocarbon compounds having no oxygen atoms). The produced hydrocarbons may be used as fuel or base oil component or chemicals or as starting components in the production of fuel or base oil components or chemicals. The hydrodeoxygenated products may also be further isomerized to isoparaffins.

One of the advantages of the present invention is that ketoacids produced from renewable materials can be upgraded to higher molecular weight hydrocarbons and/or hydrocarbon derivatives, which may be used as fuel or base oil component or chemicals or as intermediate components in the production of fuel or base oil components or chemicals.

The unreacted ketoacid monomers and other low molecular weight components such as water and $CO_2$ formed in the condensation reaction(s) may be separated from the acidified reaction product as illustrated in FIG. 3. The separation may be conducted by any conventional means such as by distillation. The unreacted ketoacid monomer is preferably recycled and combined with the feedstock of the reactor.

Another aspect of the present invention involves a method for production of hydrocarbons, the method comprising steps of increasing the molecular weight of a ketoacid using the method of the present invention to obtain a purified reaction product and subjecting the reaction product to a hydrodeoxygenation (HDO) step and optionally to an isomerization step.

The HDO catalyst employed in the hydrodeoxygenation step may comprise a hydrogenation metal on a support, such as for example a HDO catalyst selected from a group consisting of Pd, Pt, Ni, Co, Mo, Ru, Rh, W or any combination of these. The hydrodeoxygenation step may for example be conducted at a temperature of 100-500° C. and at a pressure of 10-150 bar (absolute).

Water and light gases may be separated from the HDO product with any conventional means such as distillation. After the removal of water and light gases the HDO product may be fractionated to one or more fractions suitable for use as gasoline, aviation fuel, diesel or base oil components. The fractionation may be conducted by any conventional means, such as distillation. Optionally part of the product of the HDO step may be recycled and combined to the feed of the HDO reactor.

Another aspect of the present invention involves a hydrocarbon composition obtainable by the method according to the present invention. This product may be used as fuel or base oil components or chemicals or as intermediate components in production of fuel or base oil components or chemicals.

The product of the hydrodeoxygenation step may also be subjected to an isomerization step in the presence of hydrogen and an isomerization catalyst as illustrated in FIG. 4. Both the hydrodeoxygenation step and isomerisation step may be conducted in the same reactor. The isomerisation catalyst may be a noble metal bifunctional catalyst, for example Pt-SAPO or Pt-ZSM-catalyst. The isomerization step may for example be conducted at a temperature of 200-400° C. and at a pressure of 20-150 bar (absolute).

It is preferred that only a part of the HDO product is subjected to an isomerization step, in particular the part of HDO product which is subjected to isomerization may be the heavy fraction boiling at or above temperature of 300° C.

The hydrocarbon product obtainable from the hydrodeoxygenation and/or the isomerisation step may be used as fuel or base oil components or chemicals or as intermediate components in production of fuel or base oil components or chemicals.

Generally the choice of subjecting HDO product to isomeration is highly dependable of the desired properties of the end products. In case the HDO product contains a high amount of n-paraffins, the HDO product may be subjected to isomerization step to convert at least part of the n-paraffins to isoparaffins to improve the cold properties of the end product.

EXAMPLES

Materials

Commercial grade NaOH used in the Examples was provided by J. T. Baker and commercial grade levulinic acid (97%) was provided by Sigma-Aldrich.

Example 1

Increasing the Molecular Weight of Levulinic Acid by Base Catalysed Condensation Reactions in the Presence of NaOH.

The performance of NaOH was evaluated in a batch reactor test run with a feedstock comprising 56 wt-parts of levulinic acid and 22 wt-parts of water and 22 wt-parts of NaOH. NaOH pellets and water were mixed in ratio of 1:1 by weight and the solution was allowed to cool to room temperature. The resulting NaOH solution was transferred to the reactor, which already contained the LA. The feedstock was then heated in the batch reactor to the reaction temperature given in Table 1.

The condensation reactions were conducted at temperatures of 100° C. and 120° C. and under a gauge pressure of 0.2 bar and 0.5 bar (1.2 bar and 1.5 bar absolute pressure). The reaction mixture was continuously stirred to enable uniform temperatures across the reaction vessel. Reaction was allowed to continue for 3 hours in both experiments. After the test, the reactor was allowed to cool to room temperature. In both cases the liquid yield was 97-100% (i.e. 3 to 0% by mass of the reaction products were gaseous or solid).

The quantitative amount of LA in liquid product was determined by GPC analysis. Collected sample was acidified prior to GPC analyses. The water produced during the reaction and water present in the feedstock was not included in analyses. Structures of dimers and trimers were confirmed with GC-MS.

The process conditions and product compositions of the organic (liquid) phase in base catalysed condensation reactions of levulinic acid with NaOH are presented in Tables 1 and 2.

TABLE 1

Process conditions and product yields with NaOH.

| Process conditions | | | | |
|---|---|---|---|---|
| Temp. ° C. | Pressure bar | Stirring rpm | Reaction time hours | Experiment |
| 100 | 1.2 | 400 | 3 | EX 1 |
| 120 | 1.5 | 400 | 3 | EX 2 |

TABLE 2

Product distribution in the organic phase with NaOH.

| Composition of organic phase | | | | |
|---|---|---|---|---|
| LA wt-% | Dimers wt-% | Trimers wt-% | Oligomers wt-% | Experiment |
| 36 | 14 | 47 | 3 | EX 1 |
| 24 | 9 | 61 | 6 | EX 2 |

It can be confirmed from the above results that base catalysed condensation reaction(s) of ketoacids produce ketoacid trimers and other oligomers with good selectivity and with high yield. The resulting products have a molecular weight distribution suitable for further conversion to fuel or baseoil components and/or chemicals.

The invention claimed is:

1. A method for increasing the molecular weight of a ketoacid, the method comprising:
   providing in a reactor a feedstock having at least one ketoacid, water and a base; and subjecting the feedstock to one or more base catalysed condensation reaction(s) to obtain a reaction product,
   wherein the base catalysed condensation reaction(s) is/are conducted at a temperature of at least 65° C.,
   wherein the base catalysed condensation reaction(s) is/are C-C coupling reaction(s),
   wherein a total content of dimerization, trimerization, tetramerization, pentamerization, and hexamerization products of ketoacid present in the reaction product of the one or more base catalysed condensation reaction(s), is more than 40 wt %, based on the reaction product.

2. The method according to claim 1, wherein the at least one ketoacid is a γ-ketoacid.

3. The method according to claim 1, wherein the base is a hydroxide, carbonate, or phosphate of an alkaline metal or alkaline earth metal, or a combination of these.

4. The method according to claim 1, wherein the content of the base in the feedstock is adjusted such that the pH of the feedstock is at least 8.0.

5. The method according to claim 1, wherein the content of the base in the feedstock is adjusted such that a ratio of the number of proton accepting groups provided by the base to the number of carboxylic acid groups provided by the at least one ketoacid is in the range of 1.00:1.00 to 5.00:1.00.

6. The method according to claim 1, wherein a molar ratio of the content of the base in the feedstock to the content of the at least one ketoacid in the feedstock is in the range of 1.00:1.00 to 5.00:1.00.

7. The method according to claim 1, wherein the content of the base in the feedstock is adjusted such that more than 90% (by mole) of the acid groups of the at least one ketoacid in the feedstock are deprotonated.

8. The method according to claim 7, wherein the acid groups of the at least one ketoacid in the feedstock are converted into carboxylic acid metal salt groups.

9. The method according to claim 1, wherein the content of the at least one ketoacid in the feedstock is at least 5.0 mol-%; and/or
wherein the content of water in the feedstock is at least 1.0 mol-%.

10. The method according to claim 1, wherein a mixture of at least two basic compounds is used as the base.

11. The method according to claim 1, wherein the method further comprises:
preparing the feedstock by mixing the at least one ketoacid, the base and optionally the water prior to subjecting the feedstock to the one or more base catalysed condensation reaction(s) and
wherein the preparing the feedstock is conducted at a temperature in the range of 10° C. to 55° C.

12. The method according to claim 1, further comprising:
acidifying the reaction product of the condensation reaction(s) by adding an inorganic acid or an organic acid.

13. The method according to claim 12, further comprising:
purifying the acidified reaction product by extraction, precipitation, crystallization, or liquid-liquid extraction using a solvent.

14. A method of producing hydrocarbons, comprising:
increasing the molecular weight of a ketoacid using the method according to claim 12 to obtain a reaction product, and subjecting the reaction product to a hydrodeoxygenation step and optionally to an isomerization step.

15. The method according to claim 1, wherein the at least one ketoacid is levulinic acid; and/or
wherein the base catalysed condensation reaction(s) is/are conducted at a temperature in the range of 100 to 120° C.

16. The method according to claim 1, wherein the base is a hydroxide, carbonate, or phosphate of one of Na, Li, Be, Mg, K, Ca, Sr or Ba, or a combination of these, with the hydroxide being sodium hydroxide, potassium hydroxide or lithium hydroxide or a combination of these.

17. The method according to claim 15, wherein the content of the base in the feedstock is adjusted such that the pH of the feedstock is at least 12.0.

18. The method according to claim 16, wherein the content of the base in the feedstock is adjusted such that the ratio of the number of proton accepting groups provided by the base to the number of carboxylic acid groups provided by the at least one ketoacid is in the range of 1.05:1.00 to 2.00:1.00.

19. The method according to claim 17, wherein the molar ratio of the content of the base the feedstock to the content of the at least one ketoacid in the feedstock is in the range of 1.10:1.00 to 2.00:1.00.

20. The method according to claim 1, wherein the content of the base in the feedstock is adjusted such that more than 99% (by mole), of the acid groups of the at least one ketoacid in the feedstock are deprotonated.

21. The method according to claim 1, wherein the content of the at least one ketoacid in the feedstock is at least 20.0 mol-%; and/or
wherein the content of water in the feedstock is at least 30.0 mol-%.

22. The method according to claim 1, wherein the method further comprises:
preparing the feedstock by mixing the at least one ketoacid, the base and optionally the water prior to subjecting the feedstock to the one or more base catalysed condensation reaction(s) and
wherein the preparing the feedstock is conducted at a temperature in the range of 15° C. to 45° C.

23. The method according to claim 1, further comprising:
acidifying the reaction product of the condensation reaction(s) by adding a formic acid or acetic acid.

24. The method according to claim 12, comprising:
purifying the acidified reaction product by liquid-liquid extraction using a solvent.

25. The method according to claim 1, wherein the base catalysed condensation reaction(s) is/are conducted at a temperature in the range of 100 to 120° C.

26. The method according to claim 1, wherein the reaction product comprises at least one levulinic acid trimer.

* * * * *